United States Patent [19]

Schweiger

[11] Patent Number: 4,694,021

[45] Date of Patent: Sep. 15, 1987

[54] METHOD FOR TOPICAL TREATMENT OF SCAR TISSUE

[76] Inventor: Raymond H. Schweiger, 363 S. Bonsal St., Baltimore, Md. 21224

[21] Appl. No.: 859,816

[22] Filed: May 5, 1986

[51] Int. Cl.$^4$ .......................................... A61K 31/235
[52] U.S. Cl. .................................... 514/544; 514/588; 514/949
[58] Field of Search ................................ 514/949, 544

[56] References Cited

PUBLICATIONS

Harry—Modern Cosmeticology, vol. 1, 1955, pp. 149-154.

Primary Examiner—Leonard Schenkman
Attorney, Agent, or Firm—Schwartz, Jeffery, Schwaab, Mack, Blumenthal & Evans

[57] ABSTRACT

Topical application to regions of tissue scarring of a composition comprised of several ingredients commonly used in cosmetic products, such as urea, leads to a reduction and a softening of scar tissue.

13 Claims, No Drawings

METHOD FOR TOPICAL TREATMENT OF SCAR TISSUE

BACKGROUND OF THE INVENTION

The present invention relates to a method for softening and reducing cutaneous and subcutaneous scar tissue. More specifically, the present invention relates to a method for treating scar tissue by the topical application of a specific composition directly to areas of the body where scarring has occurred, for example, as a result of trauma accompanying surgery.

Advances in plastic surgery have ameliorated the problem of scarring that occurs, both in the layers of the skin (cutaneously) and in the region beneath the skin (subcutaneously), due to trauma associated with injury or surgical intervention. Nevertheless, there was heretofore little that could be done to normalize the appearance of specific scar tissue after sufficient time has passed for significant natural reduction of scar mass to have stopped.

SUMMARY OF THE INVENTION

It is therefore an object of the present invention to provide a therapeutic method for treating scar tissue that is effective in normalizing the appearance of such tissue, even after the process of natural reduction of scar mass has ceased.

It is also an object of the present invention to provide a simple, noninvasive and relatively inexpensive method for softening and reducing both cutaneous and subcutaneous scar tissue.

In accomplishing the foregoing objects, there has been provided, in accordance with one aspect of the present invention, a method for treating scar tissue, comprising the step of topically applying, to a body region where cutaneous or subcutaneous scarring has occurred, a therapeutically effective amount of a composition comprising an argillaceous absorbent, at least one ester of p-hydroxybenzoic acid, urea, and a sulfosuccinate compound. In a preferred embodiment, the aforesaid composition is applied, to the body region where scarring has occurred, in a sufficient amount such that a 0.5 to 1 centimeter-thick layer of the composition covers substantially all of the scar-affected body region.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

It has been discovered that certain commercially-available substances, each having a common use in cosmetic products but no well-defined therapeutic effect in treating scar masses, can be employed together in topical application to effect a reduction and a softening of scar tissue, even years after the trauma which caused the scarring. Although the physiological basis for this therapeutic effect is unclear, it is believed that topical application of the above-described composition induces (or enhances) natural mechanisms for the decalcifying or breaking up of fibrous material in scar-tissue masses. Such activity would be consistent with the observation, described in greater detail below, that topical applications of a composition in accordance with the present invention lead to a reduction of cutaneous and subcutaneous scar tissue and calcified bone overgrowth following rhineoplastic surgery.

A composition useful in treating scar tissue according to the present invention preferably comprises an argillaceous material, such as China clay, colloidal kaolin, bentonite or other aluminum silicate solid, which can act both as an absorbent and a base for the composition. Fuller's Earth, a nonplastic variety of magnesium-containing kaolin, is particularly preferred in this regard.

The above-described composition further comprises urea, sometimes called "imidazolidinyl urea" in cosmetic products. Urea has been used as an antiseptic and a deodorizer in shampoos, hand creams, lotions, roll-on deodorants and other preparations. According to DeNavarre, II THE CHEMISTRY AND MANUFACTURE OF COSMETICS 322 (D. Van Nostrand Co. 1962), urea "has been used as a healing agent in both drug and cosmetic creams and lotions." No role in affecting scar tissue is known to have been ascribed to topical applications of urea, however.

A third constituent of a composition employed in the present invention is a p-hydroxybenzoic acid ester, such as methyl or p-hydroxybenzoate ("methylparaben") and propyl p-hydroxybenzoate ("propylparaben"). Such esters are widely used in cold creams, eyeliners and liquid makeup products as preservatives and antimicrobial agents, but no therapeutic activity is known to be attributed to them. In the present invention, it is preferred that both methyl and propyl p-hydroxybenzoate are present in the topically applied composition.

A composition used pursuant to the present invention should also contain coconut oil (cocamide) or one of its derivatives, all typical ingredients in skin cleansers, and a sulfosuccinate compound of the type used as wetting agents and mild detergents in shampoos and lotions.

A preferred constituent is an aromatic balsamic resin of the sort commonly included in skin-protective creams. Tincture of benzoin is illustrative of such resins, but like methyl and propyl p-hydroxybenzoate it can cause allergic skin reactions in some cases. If skin reactions do occur when scar tissue is treated in accordance with the present invention, then an intermediate layer of a hypoallergenic cream, such as FOSTRIL®, a product of Westwood Pharmaceuticals, Buffalo, N.Y., can be applied to the location of the scar mass, prior to topical application of the above-described composition, without negating the tissue-normalizing effect of the treatment. FOSTRIL® itself comprises 6.7% by weight of lauryl alcohol and 2% by weight of sulfur, relative to total weight, in a cream base and is used in treating acne.

In any event, it is preferred that the primary, urea-containing composition be applied to the region of the scar tissue in amounts sufficient to form a layer, preferably one-half to one centimeter in thickness, over substantially the entire region. "Substantially" in this context means that the therapy of the present invention does not require, for effectiveness, a total coverage of the scarred region. Nevertheless, it is preferred that the body area affected by scarring be completely covered, with a slight overlapping and tapering of the layer into surrounding regions not so affected.

To this end, it is also preferable that the composition possess a consistency permitting it to be caked onto the region where scarring has occurred. Thus, the composition preferably has the texture of a face pack or mask, as described in HARRY'S COSMETICOLOGY 103-110 (1973) the contents of which are hereby incorporated by reference. It is preferable that the composition contain enough water, inter alia, to achieve the desired "caking" consistency. A given application of the composition can then continue for between one-and-a-half and two hours, until the cakedon composition dries and hardens.

A commercially available product which is particularly preferred for use in treating scar tissue according to the present invention is MUDD ® (manaufactured by Chattem, Inc., Chattanooga, Tenn.), a face pack having a formulation (water, Fuller's Earth, disodium cocamido MIPA sulfosuccinate, tincture of benzoin, imidazolidinyl urea, methylparaben and propylparaben) which comes within the preceding description. Periodic topical applications of MUDD ®, about once daily, to a region of the nose which had been scarred, both cutaneously and subcutaneously, by major rhineoplastic surgery were associated with a reduction in the mass of scar tissue, a concomitant softening of remaining scar tissue, and a recession in calcium overgrowth which has caused an apparent thickening of the nasal bone. These effects of the therapy, following the present invention, were particularly unexpected because the surgery which caused the scarring thus treated had taken place some seven years earlier, i.e., the treatment was effective well after significant post-operative normalization of the damaged tissue had ceased.

A noticeable softening of scar tissue caused by sergery on a finger was observed with topical applications of the MUDD ® formulation, about twice a day over a period of about three weeks, some five months after the surgical procedure (i.e., when significant natural healing was still ongoing), pursuant to the present invention. The therapy in accordance with the present invention thus accelerated scar normalization during the natural healing period. In contrast to the above-summarized treatment of nasal scarring, layerings of the kaolin-containing composition within the present description onto the hand region where scarring had occurred were not preceded by an application of a layer of FOSTRIL ®, since a mild rash which had accomplished topical applications to the nasal scar tissue did not occur in the latter treatment.

What is claimed is:

1. A method for treating scar tissue, comprising the step of topically applying, to a body region where cutaneous or subcutaneous scarring or calcified bone overgrowth has occurred, a therapeutically effective amount of a first composition comprising an argillaceous absorbent, at least one ester of p-hydroxybenzoic acid, urea, and a sulfosuccinate compound.

2. A method according to claim 1, wherein said absorbent consists essentially of Fuller's Earth.

3. A method according to claim 1, wherein said ester of p-hydroxybenzoic acid is at least one from the group consisting of methyl p-hydroxybenzoate and propyl p-hydroxybenzoate.

4. A method according to claim 3, wherein said first composition further comprises an aromatic balsamic resin.

5. A method according to claim 4, wherein said resin further comprises tincture of benzoin.

6. A method according to claim 5, wherein (a) said absorbent consists essentially of Fuller's Earth and (b) said first composition comprises methyl p-hydroxybenzoate and propyl and p-hydroxybenzoate.

7. A method according to claim 6, wherein natural reduction of scar mass in said body region has ceased.

8. A method according to claim 1, wherein said amount of said composition applied to said body region is sufficient to form a layer of said composition which covers substantially all of said region.

9. A method according to claim 8, wherein said layer has a thickness between about 0.5 and 1 centimeter.

10. A method according to claim 8, further comprising, prior to said topical application of said first composition, the step of applying to said body region an amount of a second composition which is sufficient to form a layer of said second composition covering substantially all of said region, said second composition consisting essentially of a hypoallergenic cream.

11. A method according to claim 10, wherein said second composition consists essentially of a 6% by weight of lauryl alcohol and 2% by weight of sulfur in a cream base, weight percentage being relative to the total weight of said second composition.

12. A method according to claim 1, wherein natural reduction of scar mass in said body region has ceased.

13. A method according to claim 1, wherein said first composition comprises an argillaceous absorbent, an ester of p-hydroxybenzoate acid, urea and disodium cocamido MIPA-sulfosuccinate.

* * * * *